United States Patent [19]
Lynch et al.

[11] Patent Number: 5,998,139
[45] Date of Patent: Dec. 7, 1999

[54] ASSAY FOR DETERMINATION OF NEURONAL ACTIVITY IN BRAIN TISSUE

[75] Inventors: Gary Lynch; Richard Granger; Christine M. Gall, all of Irvine; Linda C. Palmer, Newport Beach, all of Calif.

[73] Assignee: The Regents of the University of California, Oakland, Calif.

[21] Appl. No.: 08/838,769

[22] Filed: Apr. 10, 1997

[51] Int. Cl.$^6$ ............................... C12Q 1/68; C12Q 1/08; C07H 21/04

[52] U.S. Cl. ......................... 435/6; 435/40.52; 435/40.5; 536/24.31

[58] Field of Search ........................ 435/6, 40.52, 40.5; 536/24.31; 935/77, 78

[56] References Cited

PUBLICATIONS

Creese, I. et al. (1976) "Dopamine Receptor Binding Predicts Clinical and Pharmacological Potencies of Antischizophrenic Drugs," *Science* 192: 481–483.

Curran, T., et al., (1987) "Isolation and characterization of the C–fos (rat) cDNA and analysis of post–translational modification in vitro," *Oncogene* 2: 79–84.

Fuxe, K. et al., (1991) "Computer–assisstedImage Analysis Techniquest allow a Characterization of the Compartments within the Basal Ganglia. Focus on Functional Compartments Produced by d–Amphetamine Activation of the c–fos Gene and its Relationship to the Glucocorticoid Receptor," *J. Chem. Neuro.* 4: 355–372.

Gall et al., (1994) "Seizures increase basic fibroblast growth factor mRNA in adult rat forebrain neurons and glia," *Mol. Brain Res.* 21: 190–205.

Graybiel, A., et al. (1990) "Amphetamine and cocaine induce drug–specific activation of the c–fos gene in striosome–matrix compartments and limbic subdivisions of the striatum," *Proc. Natl. Acad. Sci. USA*, 87: 6912–6916.

Greenberg et al. (1986), "Stimulation of Neuronal Acetylcholine Receptors Induces Rapid Gene Transcription," *Science* 234: 80–83.

Hess et al. (1997) "Changes in c–fos mRNA Expression in Rat Brain during Odor Discrimination Learning: Differential Involement of Hippocampal Subfields CA1 and CA3," *J. Neurosci.* 15: 4780–4795.

Hess, U.S. et al., (1995) "Regional Patterns of c–fos mRNA Expression in Rat Hippocampus Following Exploration of a Novel Environment versus Performance of a Well–Learned Discrimination," *J. Neuro.* 15(12): 7796–7809.

Lauterborn, J.C. et al., (1993) "In situ hybridization Localization of choline acetyltransferase mRNA in adult rat brain and spinal cord,"*Mol. Brain Res.* 17: 59–69.

Morgan and Curran (1991) "Stimulus–transcription coupling in the nervous system: involvement of the inducible proto–oncogenes fos and jun," *Annu. Rev. Neurosci* 14: 421–451.

Palmer, L.C., et al. (1996) "Positive Modulators of AMPA Receptors Increase Neuronal Activity in Neocortex Relative to Striatum: An Adjunct Treatment for Schizophrenia?" *Soc. for Neuro.* 22: Abstract 657.3.

Sagar, et al. (1988) "Expression of c–fos Protein in Brain: Metabolic Mapping at the Cellular Level," *Science* 240: 1328–1331.

Wisden et al., (1990) "Differential Expression of Immediate Early Genes in the Hippocampus and Spinal Cord," *Neuron* 4: 603–614.

Steiner et al, "Dynorphin opioid inhibition of cocaine–induced, D1 dopamine receptor mediated immediate early gene expression in the striatum", *J. Comp. Neurol.* 353:200–212, 1995.

Rueb, et al., "HeLa D98/AH–2 Studied By Chromosome Painting and Conventional Cytogenetical Techniques," *Chromosoma* (Jul. 1993) vol. 102, No. (7):473–477.

Hames et al. editors of Nucleic Acid Hybridization: A Practical Approach pp. 17–30 and 179–184, 1985.

Valentino et al. editors of In Situ Hybridization: Applications to Neurobiology. pp. 3–24, 1989.

Hames et al. Editors Gene Probes 2: A Practical Approach pp. 183–210, 246–247, 1995.

Amersham Catalog pp. 98–121 and 214–215, 1994.

Oncogene Science Catalog, pp. 86–97, 1992.

Lamprecht et al. NeuroReport 7:289–293, Dec. 1995.

Fosnaugh et al. J. Neurochem. 64:2377–2380, May, 1995.

MacGibbon et al. Mol. Brain. Res. 23:21–32, Apr. 1994.

Semba et al. Neurochem. Intl. 29:435–442, Oct. 1996.

*Primary Examiner*—Jeffrey Fredman
*Attorney, Agent, or Firm*—Karl Bozicevic; Dianna L. DeVore; Bozicevic, Field & Francis LLP

[57] ABSTRACT

The activation of neurons in specific areas of a mammalian brain are determined by measurement of levels of mRNA following administration of an agent that potentially affects neuronal activity. Differential levels of mRNA caused by an agent can be measured, as can the specific distribution of the alteration of neuronal activity. Many mental disorders are associated with the abnormal function of a particular area of the brain. The present invention allows the determination of which area of the brain, if any, is affected by an administered agent. Accordingly, the invention provides a valuable tool for assaying compounds as potential therapeutic agents.

6 Claims, 3 Drawing Sheets

| Animal | Model of | Treatment |
|---|---|---|
| Rat; chronic methamphetamine | Methamphetamine abuse; methamphetamine-induced psychoses; schizophrenia | Antipsychotic drugs such as clozapine |
| Stressed rats / Rats in anxiety-producing situation such as elevated-plus maze | Anxiety; depression | Antidepressants (e.g. benzodiazepines), 5HT reuptake inhibitors (prozac); 5HT antagonists (buspirone) |
| SHR (spontaneously hypertensive rats) | Attention-deficit hyperactivity disorder (ADHD) | Ritalin |
| Limbic electrical stimulation | Epilepsy | Antiepileptic drugs such as gabapentin, vigabatrin |

ASSAY FOR DETERMINATION OF NEURONAL ACTIVITY IN BRAIN TISSUE

Material described herein was developed, at least in part, with funds from the Research Scientist Development Award No. MH00974 and the National Institutes of Health via Grant No. HD24236 and the government may have certain rights in this material.

FIELD OF THE INVENTION

This invention relates to an assay for determining neuronal activity in brain tissue and the use of this assay in determining the action of agents on brain tissue.

BACKGROUND OF THE INVENTION

Neuronal activation has been associated with a number of normal biological processes, such as the use of memory in learning behaviors and responsiveness to sensory stimuli (Sharp et. al. (1989) J. Comp. Neurol. 284: 621–36). Identification of changes in neuronal activation has allowed the association of behavioral and physiological activity with certain regions of the mammalian brain. This technique has been used to identify brain regions active in normal biological processes such as male sexual behavior (Bialy and Kaczmarek (1996) Acta. Neurobiol. Exp. 56: 567–77), activation of neuroendocrine systems (Hoffman et. al. (1993) Front. Neuroendocrinol. 14: 173–213), and the physiological response to injury (Dubner and Ruda (1992) Trends Neurosci 15: 96–103).

Neuronal activation has also been implicated in abnormal biological processes. The ability to measure neuronal activity in mammalian brain tissue has allowed the association of regions of the brain with particular disorders. For example, characteristic patterns of neuronal activation in specific frontal lobe and basal ganglia circuits are observed in obsessive compulsive disorder (Otto (1992) Psychiatr. Clin. North Am. 15: 825–48). Studies examining mammalian models for Parkinson's disease have found that neuronal activities of the caudate nucleus decreased, activity of the pars reticula of the substantia nigra and the internal segment of the globus pallidus increased, and neurons of the ventromedial nucleus of the thalamus depressed markedly (Yoshida M (1993) Adv Neurol 60: 71–77). Imaging studies and pathological reports suggest that neuronal activity may be altered in certain temporal limbic regions (Reynolds G. P. (1989) Br. J. Psychiatry 155: 305–16).

A great deal of evidence has linked neuronal activation events to the regulation of gene expression. The expression of certain genes has been found to vary dramatically upon neuronal activation. Detecting levels of expression of these genes may therefore be useful as an indirect determination of neuronal activity in brain tissue.

Induction of Immediate-Early Genes as an Indicator of Nueronal Activation

The correlation between the expression of immediate-early genes and neuronal activation could allow measurement of expression of these genes to indirectly indicate neuronal activation. For example, the expression of the proto-oncogene c-fos has demonstrated significant potential as a tool for determining neuronal activation. Depolarization of neurons rapidly stimulates the transcription of c-fos, leading to a dramatic and specific increase of c-fos expression in activated neurons (Greenberg et.al. (1986); Science 234: 80–3; Hunt et. al. (1987) Nature 328: 632–4; Morgan et. al. (1987) Science 237: 192–7). This increase in c-fos expression occurs in neurons in response to many different activation mechanisms, including stimulation by growth factors or neurotransmitters, polysynaptic activation, or water deprivation (Sagar et. al. (1988) Science 240: 1328–31).

The efficacy of using c-fos mRNA induction to identify specific or lower level neuronal activation, however, remained unclear. Detectable changes in mRNA levels upon neuronal activation remained diffuse or too subtle to measure by the available procedures. For example, studies examining mRNA expression in learning behaviors found no difference in the induction of a number of immediate-early genes, including c-fos (Wisden et. al. (1990) Neuron 4: 603–614). These methods thus limited the use of c-fos in experiments requiring more sensitivity and specificity.

There is a need for an assay that can accurately determine subtle neuronal activation differences in brain tissue of animals treated with introduced agents. Information on the induction or depression of neuronal activity by introduced agents may identify specific locational effects of these agents in normal subjects and in subjects displaying a particular pathological or psychological state. The identification of agents that affect the neuronal activity within specific brain regions is valuable for determining the predicted efficacy of potential therapeutic agents.

SUMMARY OF THE INVENTION

Treatment of a subject animal with different neuroactive drugs reliably yields different patterns of mRNA activation in the brain tissue of these animals. The present invention allows accurate detection of brain activity associated with the administration of an agent to brain tissue, including identification of a specific area or areas of the brain in which the activity takes place.

The assay is carried out using a control animal to which no agent is administered or a previously prepared standard and a subject animal treated with the agent of interest. The animals are sacrificed and levels of mRNA activation are measured in brain cells in specific regions of the brain by hybridization technology wherein the mRNA is associated with neuronal activity. By comparing the levels of measured gene activity in specific regions of the brain with the standard or control animals, it is possible to determine the effect of the agent on brain activity for each of these areas.

A standard that may be used in this assay is prepared by examining the mRNA levels in a statistically significant number of animals, treated or untreated. This standard may be determined using probes that hybridize to mRNA associated with neuronal activity.

An object of the invention is to provide a method of assaying brain activity induced by the administration of a particular compound.

Another object is to provide such an assay which comprises in situ hybridization of a mRNA of brain cells to determine brain activity in certain areas of the brain.

An advantage of the invention is that it makes it possible to determine the specific regions of the brain which are affected by a given compound.

In one embodiment of the invention, the sequences used for in situ hybridization are selected from the group consisting of c-fos, c-jun, junD, zif268, egr2, nurr77, c-myc, and arc.

Another embodiment of the invention focuses on the use of c-fos mRNA hybridization.

In another embodiment of the invention, the subject animals are neurophysiologically and psychologically normal.

In another embodiment of the invention, the subjects are affected by a pathological or psychological state and are treated with a given agent.

In another embodiment of the described assay method the c-fos mRNA in situ analysis is used to determine changes in neuronal activity in brains from subjects affected by a pathological or psychological state treated with a given agent, and this is compared to changes in neuronal activity in comparable subjects treated with a different agent.

In another embodiment of the invention, the c-fos mRNA in situ analysis is used to determine changes in neuronal activity in brains from subjects affected by a pathological or psychological state treated with a given agent, and this is compared to a standard for c-fos activity.

In another embodiment of the invention, the agent is labeled to allow the physical tracking of the agent within the brain cells.

In another embodiment of the invention, the mRNA analysis is carried out using a test kit containing materials necessary for performing the assay.

Other aspects and potential uses of the invention will become apparent from the following detailed description and claims.

DETAILED DESCRIPTION

Before the methods of the invention are described, it is to be understood that the invention is not limited to these particular methods. The terminology used herein is for the purpose of describing particular embodiments only, and is not intended to be limiting since the scope of the present invention will be limited only by the appended claims.

As used in this specification and the appended claims, the singular forms "a", "an", and "the" include plural references unless the context clearly dictates otherwise. Thus, for example, references to "an agent" includes mixtures of such agents unless otherwise specified. References to "a method" may likewise include one or more methods as described herein and/or which will become apparent to those persons skilled in the art upon reading this disclosure or so forth.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated by reference for the purpose of disclosing and describing the particular information for which the publication was cited. The publications discussed are provided solely for their disclosure prior to the filing date of the present application. Nothing herein is to be construed as an admission that the invention is not entitled to antedate such disclosure by virtue of prior invention.

Definitions

"Physiologically normal" animals are animals that are healthy and typical of their particular species with respect to brain function and response to exogenous stimuli.

"Pathological" animals are animals that display an abnormal physical condition. The term "pathological" includes, but is not limited to, pathologies that specifically affect neuronal activity.

"Psychologically normal" animals are animals that display normal sociological, mental and behavioral traits that are typical of their particular species.

"Psychologically abnormal" animals are animals that exhibit traits that differ from "psychologically normal" animals.

"Clinical state" means any identifiable clinical syndrome, desirable or undesirable. "Clinical states" may include, but are not limited to, pathological disease states, identifiable abnormal psychological states, and other identifiable behavioral states such as addiction.

"Neuronal activity" or "change in neuronal activity" as described herein refers to either neuronal activation or neuronal depression, specifically as measured by a change in c-fos mRNA levels.

"Agent" refers to a substance or stimuli that is introduced to an animal for purposes of the assay. The term "agent" may refer to a single substance or stimuli, or a combination of two or more substances and/or stimuli.

"Agent" may be, but is not limited to, a proposed or known therapeutic agent for treating a clinical state, or a combination of such proposed therapeutic agents.

"Subject animals" are non-human donor animals that supply the brain tissue used in the methodology of the assay. The general term "subject animal" includes animals that have not been treated with an agent and do not display a physiological or psychological clinical state, animals that have been treated with an agent and display a pathological or psychological clinical state, and animals that have not been treated with an agent that display a pathological or psychological clinical state. Preferably the subject animals are mammals.

"Control animals" or "control subjects", which are used interchangeably in this application, are animals having the same disease or non-disease state as the subject animal that are mock treated for comparative purposes. Alternatively, control animals are animals having a different disease state than the subject animals that are mock treated for comparative purposes.

"In situ mRNA hybridization" means a technique in which levels of mRNA are examined directly in tissue samples. mRNA is examined in tissue sections using a hybridization method for recognizing the message of interest.

A "standard for neuronal activity" or "standard" for purposes of the described assays is an averaged compilation of measurements of mRNA levels in the brain regions of control animals. The standard is compiled from a statistically significant number of control animals.

An "mRNA associated with neuronal activity" is any mRNA whose expression is specific and indicative of neuronal activation. These mRNAs include but are not limited to c-fos, c-jun, junD, zif268, egr2, nurr77, c-myc, and arc.

A "genetic sequence which hybridizes to mRNA associated with neuronal activity" is any sequence of nucleotides or nucleosides that will specifically hybridize to the above defined mRNA moieties under stringent hybridization conditions. These sequences may encompass the entire sequence corresponding to the mRNA of interest, or to a fragment specific enough to selectively hybridize to a particular mRNA, including sequences of at least 15 bases in length.

Assay in General

The assay of the invention is carried out by performing hybridization of small mRNA on genes which are expressed in the brain tissue when the tissue cells are activated. For example, in situ hybridization of c-fos mRNA is carried out. After performing the in situ hybridization on the brain tissue of a control animal the in situ hybridization is performed on the brain tissue of an animal which has been treated with an agent which is believed to have an effect on one or more specific areas of the brain. After the two in situ hybridizations are performed they are compared, and by noting differences in the two it is possible to determine what areas of the brain, if any, are specifically affected by the agent administered to the test animal. Specifically, the comparison of the two in situ hybridizations will be indicative of the induction or suppression of neuronal activity associated with the agent administered to the test animal as compared with the control animal. The assay provides information not only with respect to the level of suppression or induction of neuronal activity but with respect to the specific region of the brain which is affected. For example, the assay can be separately performed on specific areas of the brain such as the following: dorsomedial striatum, ventrolateral striatum, orbitofrontal cortex, somatosensory cortex, or motor cortex.

The assay method of the present invention can also be carried out without the use of a control animal test. This can be done by performing the in situ hybridization on brain tissue of a test animal which has had administered to it a test compound. After this in situ hybridization assay is carried out the results are compared with a standard which has been developed based on administering the assay to a statistically significant number of test animals which have no agent administered to them. By comparing the results to the standard it is possible to carry out an analysis of the results which is indicative of the induction or suppression of neuronal activity associated with the agent administered to the animal.

An important aspect of the invention would be to carry out assays of the invention on a wide range of different drugs used in the treatment of mental disorders. The drugs would then be specifically labelled indicating that the drug had been tested for the assay of the present invention and had been found to either induce or suppress neuronal activity in a specific area or areas of the brain.

Subject and Control Animals

Subject animals may be physiologically and psychologically normal, or pathologically and/or psychologically abnormal. Subject animals may be any non-human mammal, including but not limited to mice, rats, rabbits, dogs, cats, and primates. The animals used as subject animals may vary with the purpose of the use of the invention. Since the response a particular mammal displays may due in part to differences in complexity of their brains, the subject animals may vary depending on the brain region of interest.

Figure 1:
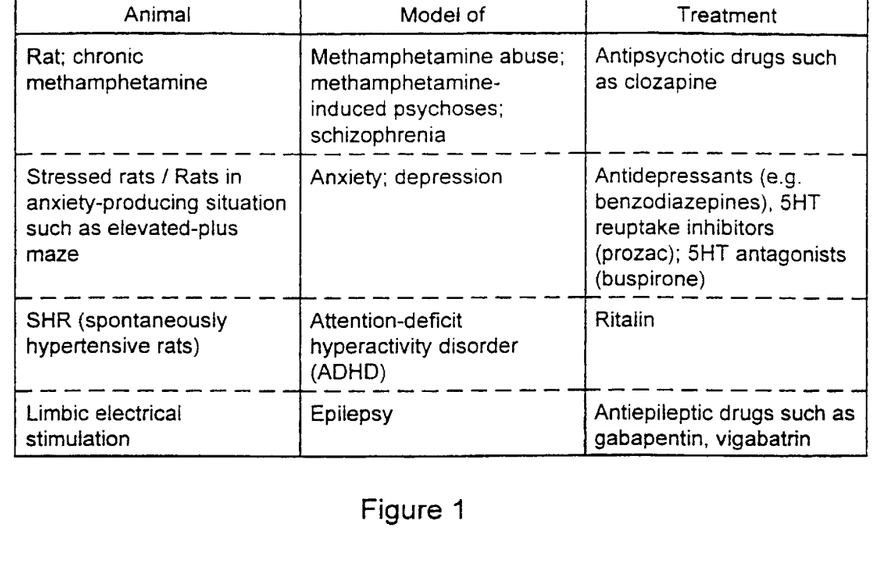
FIG. 1 is a chart of animal models for particular human clinical states and the agents that are known treatments for these clinical states.

The mammal used as subject animal may also depend upon the best animal model for a human disease state. For example, a rat on chronic methamphetamine that displays methamphetamine-induced pathologies such as hyperactivity is a useful animal model for human chronic methamphetamine abusers. In addition, rats on chronic methamphetamine are a good animal model for schizophrenia, since most human methamphetamine abusers acquire symptoms of schizophrenia and often become clinically schizophrenic. In testing potential therapeutic agents for human schizophrenia or methamphetamine addiction, rats treated with chronic methamphetamine would be used as a subject animal (FIG. 1).

Control animals are animals of the same species as their respective subject animals. Control animals may be physiologically and psychologically normal, or pathologically and/or psychologically abnormal. The control animals used in each assay will depend in part on the purpose of the assay. An assay to determine effect of an agent on normal brain tissue may use a physiologically and psychologically normal control subject. An assay to determine effects of an agent on pathological or psychologically abnormal subjects may use a physiologically and psychologically normal control subject, a control subject with the same clinical state as the treated subject, a pathological or psychologically abnormal subject not exhibiting the same clinical state as the treated subject, or any combination of these. Control subjects may also include the above described animals treated with any vehicle used in the introduction of the agent to the treated animal.

Agents

Identification of an effect of an agent in brain regions associated with a particular pathology may have great value in determining the potential efficacy of a given agent. It provides a method for in vivo testing to identify both the site of activity of proposed therapeutic agents and the level of activity in the identified regions. Labeling and tracking the agent within the brain tissue can correlate delivery of the agent to specific neurons with the effect of the agent on neuronal activity.

Identification of neuronal activity in the brain regions not involved in the clinical state of interest may also be useful, as this information could be predictive of potential side effects of proposed therapeutic agents.

The agents used in the assay to determine changes in neuronal activity in normal brain tissue may include: 1) agents with known neurophysiological effects, 2) agents in which a change in neuronal activity is predicted, or 3) agents in which a neurological effect is not predicted.

Agents with known effects may be used in the assay to determine the location and intensity of the change in neuronal activity. These agents may have a beneficial effect, e.g. a therapeutic agent, or an undesirable effect, e.g. an additive substance. The use of such agents in an assay allows comparison of neuronal activity changes between these known compounds and agents predicted to affect neuronal activity.

The invention will allow the detection of changes in the levels and distribution of neuronal activity caused by proposed therapeutic agents. This information has important predictive value in determining the potential effects of a proposed therapeutic agent in humans. Comparisons of subject animals treated with the agent of interest and subject animals treated with known agents allows the identification of new therapeutic agents. Furthermore, the use of a combination of agents in an assay allows the detection of any synergism between agents. The comparison of the combined effect with each agent's single effect can predict whether a therapeutic agent is best used alone or in tandem with another agent.

The invention may also be used to identify agents that counteract the undesirable effects of known substances. Comparisons of subject animals treated with such a known agent and subject animals treated with an agent of interest allows the identification of agents that may be useful in counteracting the negative effects of certain substances in humans.

The invention may also be used to ensure that a proposed therapeutic agent that is not predicted to have an effect on neuronal activation in a specific region of the brain in fact does not. This may ensure that a therapeutic targeted for one region of the brain does not have an undesirable effect on another region. This would be especially helpful for identifying changes that would not immediately be obvious on a macroscopic or phenotypic level, but which may have dire long-term consequences for a treated subject.

The use of testing an agent for c-fos activity levels may provide an additional quality control for marketed drugs, as testing for c-fos activity can determine both the site of activity of the agent and the areas in which the agent is not having any detectable affect on brain activity. The fact that an agent has been tested for c-fos mRNA levels may be placed on the label of any commercially or experimentally available agent to indicate that it has been tested for site of activity of the agent, prevention of predicted side effects of the agent, or both.

Probes

The assay of the present invention is carried out by performing in situ hybridization assays on the cells of brain tissue in specific regions of the brain. The in situ hybridization may be carried out using sequence probes which are associated with neuronal activity. Any sequences which are preferentially expressed during neuronal activity, which neuronal activity might be activated by the administration of an agent, could be used in connection with the present invention. The expression of the immediate-early genes c-fos, c-jun, junD, zif268, egr2, nurr77, c-myc, and arc in particular are useful indicators of neuronal activation. In the preferred embodiment of the invention it has been found that c-fos mRNA is particularly useful. It should be noted that it is not necessary to use the entire c-fos mRNA sequence in order to carry out the assay of the invention. Any fragments of the sequence which are sufficiently long so as to make it possible to carry out the hybridization assay can be used. Further, variations of the sequence which are sufficiently similar to the native sequences so as to make hybridization possible can also be used. The sequences used in the hybridization assay of the present invention are sequences which are preferably labelled which label is more preferably a radioactive label.

In the preferred embodiment, the probe used for detection in the in situ hybridization analysis is a cRNA probe corresponding to positions 583–1250 of the clone pc-fos (rat)-1 (Curran et. al., supra). For detection in a brain sample from a species other than rat, the c-fos cRNA probe may be derived from the c-fos gene of the species corresponding to the brain sample.

Other types of probes may also be used for detection of c-fos in the described invention. Other c-fos probes, including full length cDNA, full-length cRNA, partial cDNA, partial cRNA, or oligonucleotide probes that recognize c-fos can also be used for in situ hybridization without departing from the spirit of the invention.

In the preferred embodiment, the c-fos cRNA probe is radioactively $^{35}$S labeled. Other methods of labeling known in the art may be used in the invention, including digoxigenin labeling, luciferase labeling, or radiolabeling with an alternative isotope.

mRNA Detection

Comparative in situ hybridization analysis to detect mRNA levels is performed as generally described in Lauterborn, J.C. et.al., (1993) Mol. Brain Res., 17:59–69.

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Efforts have been made to ensure accuracy with respect to numbers used (e.g. amounts, concentrations, particular components, etc.) but some deviations should be accounted for.

Example 1

Measurement of c-fos Expression in Physiologically Normal Subjects Treated With Pharmacological Agents Adult rats were divided into experimental and control groups. Each group received an intraperitoneal drug injection: the vehicle control group received an injection of cyclodextrin, the vehicle in which the experimental agent ampakine CX564 was dissolved (33% weight/volume concentration); the methamphetamine group received an injection consisting of the experimental agent methamphetamine (2 mg/kg dissolved in saline) and the vehicle cyclodextrin (33% weight/volume concentration); the ampakine group received an injection consisting of the experimental agent ampakine CX564 (15 mg/kg in cyclodextrin) and saline.

30 minutes after injection, the experimental and control animals were sacrificed and intracardially perfused with 4% paraformaldehyde in 0.1M phosphate buffer (pH 7.2). Brains were post-fixed for 2–4 days at 4° C. Coronal 30 μM thick tissues were cut on a freezing microtome and collected, and processed for in situ hybridization. This time point was chosen because c-fos mRNA levels have been shown to peak approximately 30 min after exposure to neuronal activating stimuli (Morgan and Curran (1991) Annu. Rev. Neurosci 14:421–51; Shin et. al. (1990) J. Neurochem. 55: 1050–1055).

To determine the relative levels of neuronal activity in brain regions of subject animals, tissue sections cut throughout the brain were subjected to in situ hybridization according to the methods of Hess et.al. (1997 J. Neurosci. 15:4780–4795, 4788). An antisense cRNA probe complementary to rat c-fos mRNA was produced, and labeled for subsequent identification. The antisense cRNA was transcribed with T7 RNA polymerase from a linearized plasmid containing rat c-fos in the presence of uridine 5'-[α-[$^{35}$S]thio]triphosphate. Hybridization was conducted at 60° C. for 37–43 hours with a cRNA probe concentration of $1 \times 10^6$ cpm/ml.

The distribution of hybridization in the sections was evaluated using emulsion autoradiography. Autoradiograms were calibrated to allow the conversion of optical density readings to cpm/25 μgram protein (Gall et.al., supra). Densitometric analysis was performed using the public domain program NIH Image, which is an image processing and analysis software system for Macintosh-type computers. This system, in combination with a compatible frame grabber card for capturing images from a camera, allows images to be scanned calibrated, filtered, measured, and rendered in exportable form. The system is available by FTP from zippy.nimh.nih.gov or from National Technical Information Services (Springfield, Va.). The Image system was extended and customized using the system's built-in Pascal-like macro language, which is also publicly available. Other systems similar to Image that are known to those skilled in the art may also be used for densitometric analysis.

Figure 2:
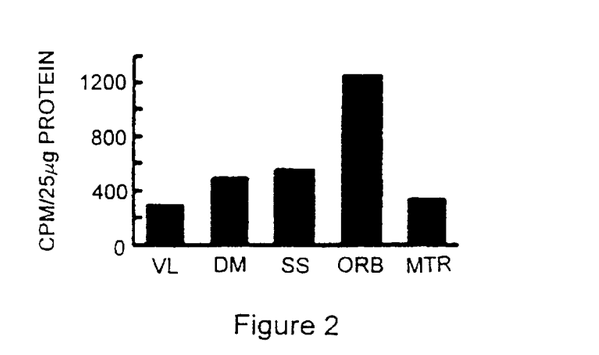
FIG. 2 is a graphic illustration of the regional differences in c-fos mRNA expression in vehicle treated rats. The bar graphs illustrate mean labeling densities in the five brain areas for an individual vehicle-treated rat. The abbreviations used in the figure are: MTR, layers II–III of motor cortex; ORB, layers II–III of orbitofrontal cortex; SS, layers III–IV of somatosensory cortex; DM, dorsomedial striatum; and VL, ventrolateral striatum.

Hybridization of the c-fos cRNA was quantified for the following brain regions: 1) dorsomedial striatum; 2) ventrolateral striatum; 3) ventral and medial orbital cortex (VO/MO); 4) primary and secondary motor cortex; and 5) primary somatosensory cortex (FIG. 2). The cortical measures included approximately layers II and III in the frontal regions (motor cortex and VO/MO) and predominantly layer IV, but with some layer III, in the somatosensory region (Swanson, (1992) Brain maps: structure of the rat brain, Elsevier, New York 1992). The three cortical regions were measured in 3–4 sections on one side of the brain at different rostro-caudal levels, and the two striatal regions were measured in two sections at the level of the columns of the fornix, on both sides of the brain. These values were averaged to determine the mean expression density per brain region per animal.

Tissue from equal numbers of subject animals in each of the three groups were processed by regional labeling density measurement for each animal normalized as percent difference within each group. Ratios in the labelling densities of different brain regions within the same animal were calculated to identify changes in relative hybridization densities. A 95% confidence level had to be reached for differences to be considered significant (p less than 0.005). Differences in expression density were given as (mean difference in %±standard deviation). The standard deviation was determined using an unpaired Mann-Whitney U test, two tailed.

Figure 3:
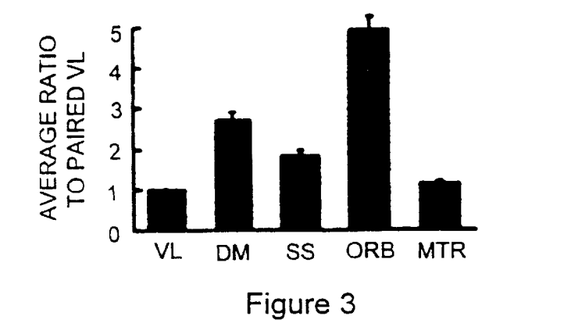
FIG. 3 is a bar graph of the group mean labeling densities for 11 vehicle rats.

Levels of c-fos mRNA varied considerably between brain regions in the vehicle control rat, and these variations were reliable across the control group (FIG. 3). Methamphetamine or ampakine treatment each had significant and consistent effects both on the level of c-fos mRNA expression in certain regions and the particular regions in which c-fos was expressed.

Figure 4:
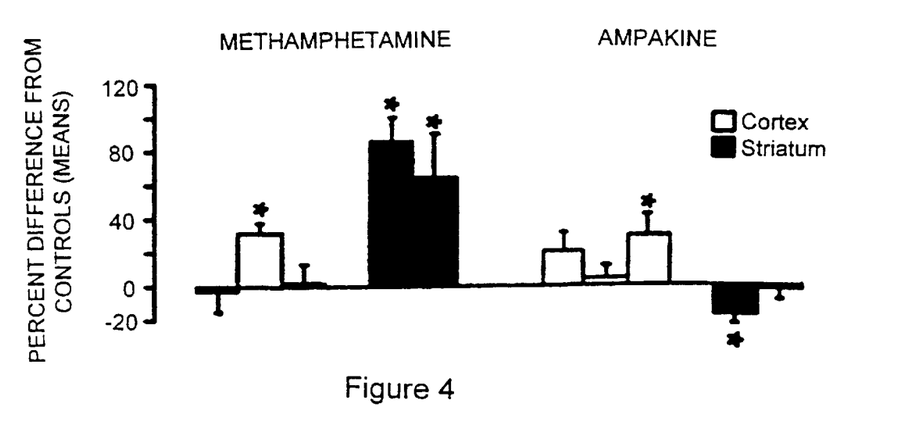
FIG. 4 is a graphic illustration of the group mean values of methamphetamine and ampakine treatment induced c-fos expression. Bar graphs illustrate the effects of methamphetamine (left) and ampakine (right) on mean labeling densities in the five examined brain regions. For each drug-treated rat, the percent difference in measurement from simultaneously processed control rats was calculated.

Methamphetamine did not significantly increase expression in somatosensory (−7%) or motor cortices (−14%) (FIG. 4). Methamphetamine did produce a sizable and significant (32±20%, P=0.0003) increase in hybridization in orbitofrontal cortex. Methamphetamine also increased the mRNA expression in the dorsomedial segment (85±51%) and the ventrolateral zone (65±85%, P=0.0014) providing qualitative confirmation for earlier reports that the drug has heterogeneous effects within striatum (Grabble et. al. (1990) Proc. Natl. Aced. Sci. U.S.A. 87: 6912–6916; Nguyen et. al. (1992) Proc. Natl. Aced. Sci. U.S.A. 89: 4270–4274; Jaber et. al. (1995) Neurosci. 65: 1041–1050). The methamphetamine amplified an already present difference in labeling densities between the two striatal sampling zones and the average within-animal ratios of dorsomedial to ventrolateral measures, although this difference did not reach statistical significance.

Differential effects of methamphetamine on c-fos mRNA expression were readily apparent in striatum and orbitofrontal cortex. The striatum of control rats reflected a gradient with labeled cells far more numerous in the dorsomedial than in the ventrolateral zone. At the cellular level, the dorsomedial segment of control animals contained more labelled cells and greater density labelling per cell than in the ventrolateral zone. Methamphetamine treatment increased c-fos mRNA expression in both of these sectors, but to a much greater extent in the dorsomedial zone. The most intensely labeled striatal site was slightly displaced from the dorsomedial "corner" of the striatum.

Methamphetamine elicited a clear increase in c-fos expression throughout the depth of the orbitofrontal complex without causing evident change in the more dorsal and lateral zones. Control rats displayed a more intense c-fos mRNA expression in orbitofrontal than in dorsolateral cortical segments.

In contrast to methamphetamine treatment, ampakine treatment decreased c-fos mRNA levels in dorsomedial striatum (17±18%, P<0.05), but had no effect in ventrolateral striatum (FIG. 4). The mean and median ratios of c-fos mRNA expression in ampakine treated rats versus vehicle treated rats was close to 1.00 for ventrolateral striatum. The ampakine treatment also led to a statistically significant increase in expression within the somatosensory cortex (30±41%; P=0.0336) and a trend for increased expression within motor cortex (21±36%). Ampakine did not appear to significantly change levels of c-fos mRNA in the orbitofrontal cortex.

Within-rat comparisons for the vehicle control group revealed that labeling densities of c-fos mRNA in the somatosensory and motor cortices were well correlated with those in ventrolateral striatum (r=0.83, r=0.92, respectively) but less well with the values for dorsomedial striatum (r=0.56, r=0.60). This pattern also held for the ampakine group, with a high correlation of measures from somatosensory and motor cortex with those from ventrolateral (r=0.90, r=0.90) but not dorsomedial (r=0.61, r=0.54) striatum. This is likely due to the closer anatomical relationship of sensorimotor cortex to the lateral aspects of the striatum than to the limbic-, visual-, and cingulate-influenced dorsomedial zone (McGeorge and Faull (1989) Neurosci. 29: 503–537).

Figure 5:
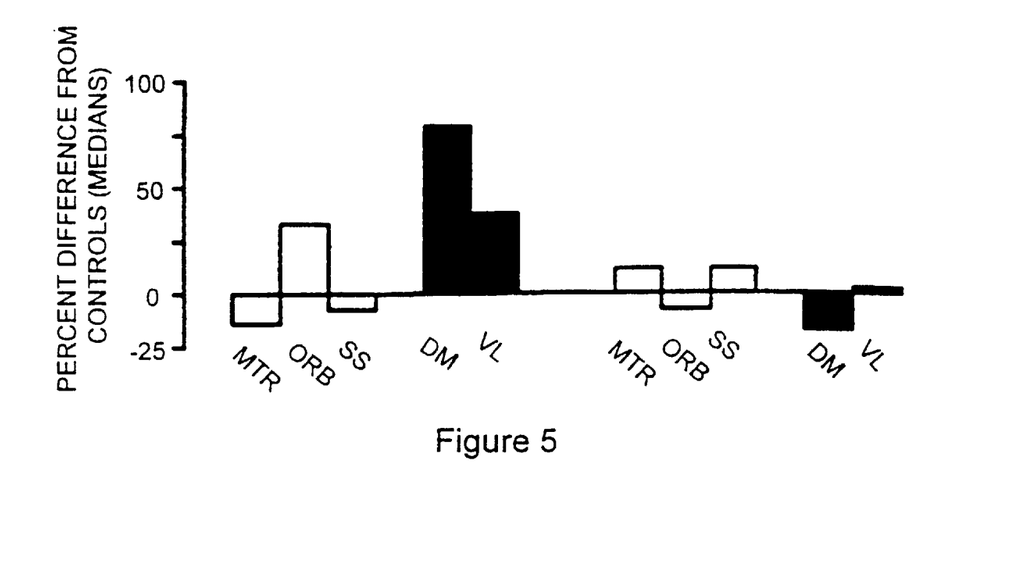
FIG. 5 is a bar graph as per FIG. 4 but showing the group median values.
Figure 6:
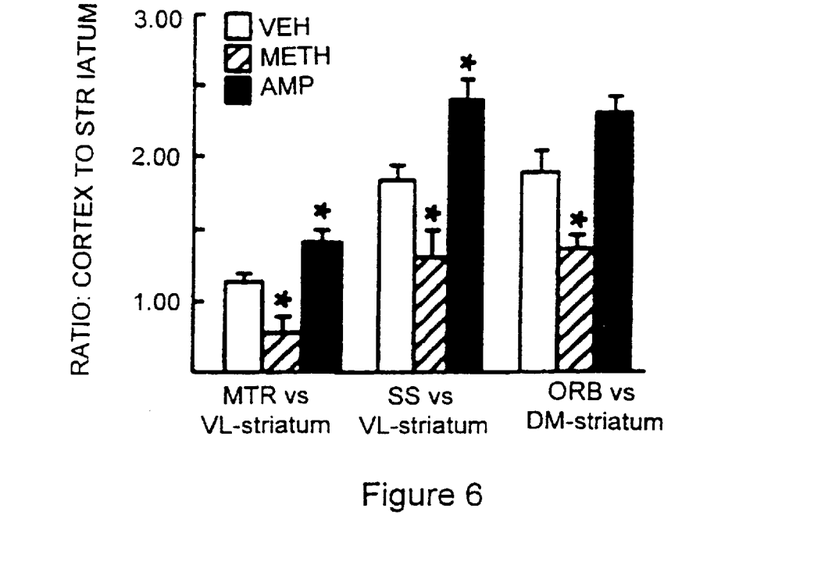
FIG. 6 is a graphic illustration of the corticostriatal c-fos expression ratios for vehicle-treated, methamphetamine-treated, and ampakine-treated rats.

The high correlations of expression allowed for rat by rat comparisons of the balance of c-fos expression in neocortex versus striatum (FIG. 5). This balance was shifted in favor of the neocortex in the ampakine group as compared to the control group, i.e. the ratios of somatosensory cortex to ventrolateral striatum and motor cortex to ventrolateral striatum were greater in ampakine-treated rats (55%, P±0.0104; 27%, P±27%, respectively). Measures of the orbitofrontal cortex were not tightly correlated with those of either dorsomedial or ventrolateral striatum in control rats (r=0.60, r=0.72), but were more closely related to those of dorsomedial (r=0.87) than ventrolateral (r=0.53) striatum in the ampakine group. The correlations between somatosensory and motor cortex labeling with ventrolateral striatal labeling in the methamphetamine group were low (r=0.24, r=0.39) and were similar to those with the dorsomedialstriatal zone (r=0.37, r=0.43).

As a result, the cortex/ventrolateral striatum ratios for the methamphetamine group were more variable but still significantly lower than control values (P=0.0281 and P=0.0104). The ampakine group displayed a greater correlation between orbitofrontal cortex and dorsomedial striatum than ventrolateral striatum in the methamphetamine animals, but the orbitofrontal/striatum ratio was significantly lower than in the methamphetamine group. (P<0.01)

Example 2

Comparison of c-fos Expression Induced by Pharmacological Agents on Subjects Displaying an Abnormal Neurophysiological Pathology Treated With Pharmacological Agents Subject animals used in the following example are adult rats exhibiting a phenotype analogous to a human neuropathology, such as schizophrenia. These adult rats are divided into five sets of subject animals: a set receiving one experimental agent (agent 1); another set receiving a different experimental agent (agent 2); a control set receiving the vehicle in which agent 1 is dissolved; a control set receiving the vehicle in which agent 2 is dissolved; and a set of untreated animals. A final control group is a set of untreated, physiologically normal adult rats.

Each treated set receives an intraperitoneal drug injection of the appropriate agent and/or vehicle. 30 minutes after injection of the treated groups, all subject animals are sacrificed, and their brains processed for in situ hybridization as previously described (Gall et.al. (1994) Mol. Brain Res., 21: 190–205).

Measurement of levels of c-fos mRNA are examined to determine the effect of the experimental agents on neuronal activity in the animals models for this disease. The following comparisons between groups are made: 1) comparison between each experimental agent set and the untreated, physiologically abnormal animal to determine the effect of the agent on the neuronal activity in affected animals; 2) comparison between each experimental agent and the untreated, physiologically normal animal to determine the expected efficacy of each agent on the affected animal; and 3) comparison between the experimental groups to compare expected efficacy of agent 1 and agent 2. Control animals treated with the vehicles will be examined to ensure that detectable differences in the neuronal activity of the subject animals arise from the experimental agent.

Tissue sections cut throughout the brain are subjected to in situ hybridization according to the methods of Hess et.al. (1997 J. Neurosci. 15:4780–4795, 4788). An antisense cRNA probe complementary to rat c-fos mRNA is produced, and labeled for subsequent detection. Probes are labeled by the incorporation of radioactively-labelled nucleosides.

The distribution of hybridization in the sections is evaluated using emulsion autoradiography. Densitometric analysis is performed using the public domain program NIH Image. Autoradiograms are calibrated to allow the conversion of optical density readings to cpm/25 microgram protein (Gall et.al., supra).

Hybridization of the c-fos cRNA is quantified for the following brain regions: 1) dorsomedial striatum; 2) ventrolateral striatum; 3) ventral and medial orbital cortex (VO/MO); 4) primary and secondary motor cortex; and 5) primary somatosensory cortex. (FIG. 2) The cortical measures include approximately layers II and III in the frontal regions (motor cortex and VO/MO) and predominantly layer IV, but with some layer III, in the somatosensory region (Swanson, (1992) Brain maps: Structure of the rat brain, Elsevier, N.Y. 1992). The three cortical regions are measured in 3–4 sections on one side of the brain at different rostro-caudal levels, and the two striatal regions were measured in two sections at the level of the columns of the fornix, on both sides of the brain. These values are averaged to determine the mean expression density per brain region per animal.

Tissue from equal numbers of subject animals in each of the three groups are processed by regional labeling density measurement for each animal normalized as percent difference within each group. Ratios in the labelling densities of different brain regions within the same animal are calculated to identify changes in relative hybridization densities. A 95% confidence level has to be reached for differences to be considered significant (p less than 0.005). Comparisons between subject animals is done as described in Example 1.

Although the invention has been described with reference to the presently preferred embodiments, it should be understood that various modifications can be made without departing from the spirit of the invention. Accordingly, the invention is limited only by the following claims.

What is claimed is:

1. A method comprising the steps of:

providing a non-human control animal displaying an abnormal neurophysiological pathology;

performing in situ hybridization with a genetic sequence which hybridizes to an mRNA associated with neuronal activity wherein the hybridization is performed on brain cells of the non-human control animal;

providing a non-human test control animal displaying an abnormal neurophysiological pathology;

treating the non-human test animal with a drug;

performing in situ hybridization with a genetic sequence which hybridizes to an mRNA associated with neuronal activity wherein the hybridization is performed on brain cells of the non-human test animal which has been treated with the drug; and comparing hybridization in the non-human control animal with hybridization in the non-human test animal and thereby determining the effect of the drug on neuronal activity associated with a particular abnormal neurophysiological pathology and particular area of brain tissue.

2. The method of claim 1 wherein the neuronal activity is examined for any of the following brain regions: dorsomedial striatum, ventrolateral striatum, orbitofrontal cortex, somatosensory cortex, or motor cortex.

3. The method of claim 1 wherein the genetic sequence which hybridizes to an mRNA associated with neuronal activity is selected from the group consisting of: c-fos sequences, c-jun sequences, junD sequences, zif268 sequences, egr2 sequences, nurr77 sequences, c-myc sequences, and arc sequences.

4. The method of claim 1 wherein the genetic sequence which hybridizes to an mRNA associated with neuronal activity comprises a cDNA sequence selected from the group consisting of: c-fos sequences, c-jun sequences, junD sequences, zif268 sequences, egr2 sequences, nurr77 sequences, c-myc sequences, and arc sequences.

5. The method of claim 1 wherein the genetic sequence which hybridizes to an mRNA associated with neuronal activity comprises a fragment of the coding region selected from the group consisting of: c-fos sequences, c-jun sequences, junD sequences, zif268 sequences, egr2 sequences, nurr77 sequences, c-myc sequences, and arc sequences.

6. The method of claim 1 wherein the clinical state induced is a clinical state of depression.

* * * * *

UNITED STATES PATENT AND TRADEMARK OFFICE
CERTIFICATE OF CORRECTION

PATENT NO:      5,998,139
DATED:          December 7, 1999
INVENTOR(S):    Gary Lynch et al.

It is certified that error appears in the above-identified patent and that said Letters Patent is hereby corrected as shown below:

In Column 1, lines 4-8, please delete the paragraph "Material described herein was developed, at least in part, with funds from the Research Scientist Development Award No. MH00974 and the National Institutes of Health via Grant No. HD24236 and the government may have certain rights in this material." and insert --Materials described herein was developed, at least in part, with funds from the Office of Naval Research Grant No. N00014-89-J-1255 and the National Institutes of Health, Grant Nos. HD24236 and MH00974 and the government may have certain rights in this material.

Signed and Sealed this

Nineteenth Day of September, 2000

Q. TODD DICKINSON

*Attest:*

*Attesting Officer*          *Director of Patents and Trademarks*